(12) United States Patent
Perschbacher et al.

(10) Patent No.: US 8,126,551 B2
(45) Date of Patent: Feb. 28, 2012

(54) AV DELAY FEATURES

(75) Inventors: David L. Perschbacher, Coon Rapids, MN (US); Richard Milon Dujmovic, Coon Rapids, MN (US); Gary T. Seim, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 566 days.

(21) Appl. No.: 12/330,869

(22) Filed: Dec. 9, 2008

(65) Prior Publication Data

US 2009/0149907 A1 Jun. 11, 2009

Related U.S. Application Data

(60) Provisional application No. 61/007,634, filed on Dec. 13, 2007, provisional application No. 61/007,067, filed on Dec. 11, 2007.

(51) Int. Cl.
*A61N 1/00* (2006.01)
(52) U.S. Cl. .......................................................... 607/9
(58) Field of Classification Search ................ 607/4–28
See application file for complete search history.

(56) References Cited

U.S. PATENT DOCUMENTS

| | | | |
|---|---|---|---|
| 3,857,399 A | 12/1974 | Zacouto | |
| 4,030,510 A | 6/1977 | Bowers | |
| 4,059,116 A | 11/1977 | Adams | |
| 4,163,451 A | 8/1979 | Lesnick et al. | |
| 4,485,818 A | 12/1984 | Leckrone et al. | |
| 4,712,556 A | 12/1987 | Baker, Jr. | |
| 4,830,006 A | 5/1989 | Haluska et al. | |
| 4,856,523 A | 8/1989 | Sholder et al. | |
| 4,860,749 A | 8/1989 | Lehmann | |
| 4,890,617 A | 1/1990 | Markowitz et al. | |
| 4,920,965 A | 5/1990 | Funke et al. | |
| 4,928,688 A | 5/1990 | Mower | |
| 4,941,471 A | 7/1990 | Mehra | |
| 4,945,909 A | 8/1990 | Fearnot et al. | |
| 4,972,834 A | 11/1990 | Begemann et al. | |
| 4,998,974 A | 3/1991 | Aker | |
| 5,085,215 A | 2/1992 | Nappholz et al. | |
| 5,156,147 A | 10/1992 | Warren et al. | |
| 5,179,949 A | 1/1993 | Chirife | |
| 5,197,467 A | 3/1993 | Steinhaus et al. | |
| 5,207,219 A | 5/1993 | Adams et al. | |
| 5,282,836 A | 2/1994 | Kreyenhagen et al. | |

(Continued)

FOREIGN PATENT DOCUMENTS

EP 0033418 A1 8/1981

(Continued)

OTHER PUBLICATIONS

"International Application Serial No. PCT/US2008/013507, International Search Report mailed May 4, 2009", 4 pgs.

(Continued)

*Primary Examiner* — Scott Getzow
(74) *Attorney, Agent, or Firm* — Schwegman, Lundberg & Woessner, P.A.

(57) ABSTRACT

An atrial event and a ventricular event can be received, and an atrioventricular (AV) delay can be provided using information about the atrial and ventricular events. The AV delay can be increased after a first condition is satisfied to allow a heart to regain intrinsic control of ventricular activation, and changed after a second condition is satisfied to allow the heart to remain in intrinsic control of ventricular activation.

22 Claims, 3 Drawing Sheets

U.S. PATENT DOCUMENTS

| | | | |
|---|---|---|---|
| 5,284,491 A | 2/1994 | Sutton et al. |
| 5,292,341 A | 3/1994 | Snell |
| 5,334,220 A | 8/1994 | Sholder |
| 5,350,409 A | 9/1994 | Stoop et al. |
| 5,356,425 A | 10/1994 | Bardy et al. |
| 5,372,607 A | 12/1994 | Stone et al. |
| 5,379,776 A | 1/1995 | Murphy et al. |
| 5,383,910 A | 1/1995 | den Dulk |
| 5,395,397 A | 3/1995 | Lindgren et al. |
| 5,400,796 A | 3/1995 | Wecke |
| 5,411,524 A | 5/1995 | Rahul |
| 5,411,531 A | 5/1995 | Hill et al. |
| 5,417,714 A | 5/1995 | Levine et al. |
| 5,462,060 A | 10/1995 | Jacobson et al. |
| 5,480,413 A | 1/1996 | Greenhut et al. |
| 5,486,198 A | 1/1996 | Ayers et al. |
| 5,527,347 A | 6/1996 | Shelton et al. |
| 5,534,016 A | 7/1996 | Boute |
| 5,540,727 A | 7/1996 | Tockman et al. |
| 5,545,186 A | 8/1996 | Olson et al. |
| 5,584,864 A | 12/1996 | White |
| 5,591,215 A | 1/1997 | Greenhut et al. |
| 5,620,471 A | 4/1997 | Duncan |
| 5,626,620 A | 5/1997 | Kieval et al. |
| 5,626,623 A | 5/1997 | Kieval et al. |
| 5,700,283 A | 12/1997 | Salo |
| 5,702,424 A | 12/1997 | Legay et al. |
| 5,713,930 A | 2/1998 | van der Veen et al. |
| 5,713,932 A | 2/1998 | Gillberg et al. |
| 5,716,383 A | 2/1998 | Kieval et al. |
| 5,730,141 A | 3/1998 | Fain et al. |
| 5,741,308 A | 4/1998 | Sholder |
| 5,749,906 A | 5/1998 | Kieval et al. |
| 5,755,739 A | 5/1998 | Sun et al. |
| 5,776,164 A | 7/1998 | Ripart |
| 5,788,717 A | 8/1998 | Mann et al. |
| 5,800,471 A | 9/1998 | Baumann |
| 5,814,077 A | 9/1998 | Sholder et al. |
| 5,836,987 A | 11/1998 | Baumann et al. |
| 5,840,079 A | 11/1998 | Warman et al. |
| 5,846,263 A | 12/1998 | Peterson et al. |
| 5,861,007 A | 1/1999 | Hess et al. |
| 5,871,507 A | 2/1999 | Obel et al. |
| 5,873,895 A | 2/1999 | Sholder et al. |
| 5,893,882 A | 4/1999 | Peterson et al. |
| 5,902,324 A | 5/1999 | Thompson et al. |
| 5,951,592 A | 9/1999 | Murphy |
| 5,978,707 A | 11/1999 | Krig et al. |
| 5,991,656 A | 11/1999 | Olson et al. |
| 5,991,657 A | 11/1999 | Kim |
| 5,991,662 A | 11/1999 | Kim et al. |
| 5,999,850 A | 12/1999 | Dawson et al. |
| 6,047,210 A | 4/2000 | Kim et al. |
| 6,091,988 A | 7/2000 | Warman et al. |
| 6,122,545 A | 9/2000 | Struble et al. |
| 6,128,529 A | 10/2000 | Elser |
| 6,151,524 A | 11/2000 | Krig et al. |
| 6,233,485 B1 | 5/2001 | Armstrong et al. |
| 6,266,554 B1 | 7/2001 | Hsu et al. |
| 6,285,907 B1 | 9/2001 | Kramer et al. |
| 6,317,632 B1 | 11/2001 | Krig et al. |
| 6,351,669 B1 | 2/2002 | Hartley et al. |
| 6,411,847 B1 | 6/2002 | Mower |
| 6,411,848 B2 | 6/2002 | Kramer et al. |
| 6,421,564 B1 | 7/2002 | Yerich et al. |
| 6,430,438 B1 | 8/2002 | Chen et al. |
| 6,434,424 B1 | 8/2002 | Igel et al. |
| 6,501,988 B2 | 12/2002 | Kramer et al. |
| 6,731,983 B2 | 5/2004 | Ericksen et al. |
| 7,013,176 B2 | 3/2006 | Ding et al. |
| 7,120,490 B2 | 10/2006 | Chen et al. |
| 7,123,960 B2 | 10/2006 | Ding et al. |
| 7,142,915 B2 | 11/2006 | Kramer et al. |
| 7,184,834 B1 | 2/2007 | Levine |
| 7,203,540 B2 | 4/2007 | Ding et al. |
| 7,283,872 B2 | 10/2007 | Boute et al. |
| 7,376,461 B2 | 5/2008 | Perschbacher et al. |
| 7,460,908 B2 | 12/2008 | Krig et al. |
| 7,844,332 B2 | 11/2010 | Perschbacher et al. |
| 2001/0014817 A1 | 8/2001 | Armstrong et al. |
| 2002/0062139 A1 | 5/2002 | Ding |
| 2002/0082509 A1 | 6/2002 | Vanderlinde et al. |
| 2002/0082660 A1 | 6/2002 | Stahmann et al. |
| 2002/0087198 A1 | 7/2002 | Kramer et al. |
| 2002/0120298 A1 | 8/2002 | Kramer et al. |
| 2003/0004551 A1 | 1/2003 | Chen et al. |
| 2003/0069610 A1 | 4/2003 | Kramer et al. |
| 2003/0233131 A1 | 12/2003 | Kramer et al. |
| 2004/0077963 A1 | 4/2004 | Perschbacher et al. |
| 2004/0215249 A1 | 10/2004 | Corbucci |
| 2004/0215259 A1 | 10/2004 | Krig et al. |
| 2005/0283196 A1 | 12/2005 | Bocek et al. |
| 2006/0167508 A1 | 7/2006 | Boute et al. |
| 2006/0195150 A1 | 8/2006 | Lovett |
| 2007/0142869 A1 | 6/2007 | Perschbacher et al. |
| 2009/0149904 A1 | 6/2009 | Perschbacher et al. |

FOREIGN PATENT DOCUMENTS

| | | |
|---|---|---|
| EP | 0401962 A2 | 12/1990 |
| EP | 0617980 A2 | 10/1994 |
| EP | 0748638 A2 | 12/1996 |
| EP | 1480715 B1 | 9/2009 |
| WO | WO-00/38782 A1 | 7/2000 |
| WO | WO-00/71200 A1 | 11/2000 |
| WO | WO-00/71202 A1 | 11/2000 |
| WO | WO-2009075820 A1 | 6/2009 |

OTHER PUBLICATIONS

"International Application U.S. Application No. PCT/US2008/013507, Written Opinion mailed May 4, 2009", 9 pgs.

"Pacemaker System Guide", © 2001 Guidant Corporation, 240 pgs.

"U.S. Appl. No. 10/274,697, Interview Summary mailed Oct. 10, 2007", 2 pgs.

"U.S. Appl. No. 10/274,697, Interview Summary mailed Oct. 18, 2007", 2 pgs.

"U.S. Appl. No. 10/274,697, Interview Summary mailed Dec. 20, 2005", 4 pgs.

"U.S. Appl. No. 10/274,697, Amendment and Response filed Mar. 8, 2007 to Final Office Action mailed Mar. 11, 2006", 7 pgs.

"U.S. Appl. No. 10/274,697, Final Office Action mailed Jul. 11, 2006", 6 pgs.

"U.S. Appl. No. 10/274,697, Final Office Action mailed Nov. 17, 2005", 7 pgs.

"U.S. Appl. No. 10/274,697, Non-Final Office Action mailed Jan. 19, 2006", 4 pgs.

"U.S. Appl. No. 10/274,697, Non-Final Office Action mailed Sep. 14, 2005", 8 pgs.

"U.S. Appl. No. 10/274,697, Response filed May 15, 2006 to Non-Final Office Action mailed Jan. 19, 2006", 6 pgs.

"U.S. Appl. No. 10/274,697, Response filed Oct. 18, 2005 to Non-Final Office Action mailed Sep. 14, 2005", 9 pgs.

"U.S. Appl. No. 10/274,697, Response filed Dec. 16, 2005 to Final Office Action mailed Nov. 17, 2005", 5 pgs.

"U.S. Appl. No. 10/852,602, Non-Final Office Action mailed Mar. 9, 2006", 6 pgs.

"U.S. Appl. No. 10/852,602, Non-Final Office Action mailed Aug. 24, 2006", 7 pgs.

"U.S. Appl. No. 10/852,602, Notice of Allowance mailed Nov. 1, 2007", 4 pgs.

"U.S. Appl. No. 10/852,602, Response filed Jun. 9, 2006 to Non-Final Office Action mailed Mar. 9, 2006", 23 pgs.

"U.S. Appl. No. 10/852,602, Response filed Dec. 22, 2006 to Non-Final Office Action mailed Aug. 24, 2006", 20 pgs.

"U.S. Appl. No. 10/852,602, Response filed Dec. 30, 2005 to Restriction Requirement mailed Nov. 30, 2005", 18 pgs.

"U.S. Appl. No. 10/852,602, Restriction Requirement mailed Nov. 30, 2005", 4 pgs.

"U.S. Appl. No. 11/676,464 Notice of Allowance mailed Jul. 21, 2010", 4 pgs.

"U.S. Appl. No. 11/676,464, Final Office Action mailed Dec. 17, 2009", 6 Pgs.

"U.S. Appl. No. 11/676,464, Non-Final Office Action mailed Jun. 30, 2009", 13 Pgs.

"U.S. Appl. No. 11/676,464, Notice of Allowance mailed Mar. 30, 2010", 4 pgs.

"U.S. Appl. No. 11/676,464, Response filed Mar. 18, 2010 to Final Office Action received Dec. 17, 2009", 13 pgs.

"U.S. Appl. No. 11/676,464, Response filed Sep. 28, 2009 to Office Action mailed Jun. 30, 2009", 17 pgs.

"U.S. Appl. No. 12/325,887, Final Office Action mailed Jun. 21, 2011", 7 pgs.

"U.S. Appl. No. 12/325,887, Non Final Office Action mailed Jun. 6, 2011", 8 pgs.

"U.S. Appl. No. 12/325,887, Response filed May 5, 2011 to Non Final Office Action mailed Jan. 6, 2011", 11 pgs.

"U.S. Appl. No. 12/327,567 Non-Final Office Action mailed Sep. 22, 2010", 8 pgs.

"Prosecution File History for U.S. Appl. No. 10/852,602, filed May 24, 2004", (issued as U.S. Appl. No. 7,460,908), 97 pgs.

AV DELAY FEATURES

CROSS-REFERENCE TO RELATED APPLICATIONS

This application claims the benefit under 35 U.S.C. 119(e) of U.S. Provisional Application No. 61/007,067, filed on Dec. 11, 2007, and of U.S. Provisional Application No. 61/007,634, filed on Dec. 13, 2007, each of which are hereby incorporated by reference in their entirety.

TECHNICAL FIELD

This document pertains generally to implantable medical devices, and more particularly, but not by way of limitation, to atrioventricular (AV) delay features.

BACKGROUND

Cardiac rhythm or function management devices can include implantable devices to help maintain heart rhythm or function. Cardiac rhythm or function management devices can include pacers, defibrillators, cardioverters, cardiac resynchronization therapy (CRT), or various combinations of these or other devices. In various examples, cardiac rhythm or function management devices can sense intrinsic heart contractions, deliver pacing pulses to evoke responsive heart contractions, or deliver a shock to interrupt certain arrhythmias. In certain examples, one or more of these functions can help improve a patient's heart rhythm or can help coordinate a spatial nature of a heart contraction, either of which can improve cardiac output of blood to help meet the patient's metabolic need for such cardiac output.

OVERVIEW

In certain examples, an atrial event and a ventricular event can be received, and an atrioventricular (AV) delay can be provided using information about the atrial and ventricular events. In an example, the AV delay can be increased after a first condition is satisfied to allow a heart to regain intrinsic control of ventricular activation, and changed after a second condition is satisfied to allow the heart to remain in intrinsic control of ventricular activation.

In Example 1, a system includes an implantable medical device and a processor. The implantable medical device of Example 1 can include an atrial sensing channel configured to receive an atrial event and a ventricular sensing channel configured to receive a ventricular event including at least one of a ventricular paced event or a ventricular sensed event. The processor of Example 1 can include a processor configured to provide an atrioventricular (AV) delay using information from the atrial sensing channel and the ventricular sensing channel, wherein the processor is configured to increase the AV delay from a first AV delay to a first extended AV delay after a first condition is satisfied to allow a heart to regain intrinsic control of ventricular activation, and wherein the processor is configured to change the AV delay from the first extended AV delay to a second extended AV delay after a second condition is satisfied to allow the heart to remain in intrinsic control of ventricular activation. In Example 1, at least one of the first extended AV delay or the second extended AV delay violates a constraint established using a maximum tracking rate (MTR) and a post ventricular atrial refractory period (PVARP).

In Example 2, the first condition of Example 1 optionally includes at least one of an occurrence of a specified number of cardiac cycles, a passing of a specified period of time, or an occurrence of a ventricular sensed event at the first AV delay.

In Example 3, the specified number of cardiac cycles of any one or more of Examples 1-2 optionally includes a preset number of cardiac cycles configured to allow a regular chance to cease ventricular pacing, and wherein the specified period of time includes a preset time interval configured to allow a regular chance to cease ventricular pacing.

In Example 4, the second condition of any one or more of Examples 1-3 optionally includes an occurrence of a specified number of ventricular sensed events before a specified number of ventricular paced events at the first extended AV delay.

In Example 5, the second condition of any one or more of Examples 1-4 optionally includes a single ventricular sense event before the specified number of ventricular paced events at the first extended AV delay, wherein the specified number of ventricular paced events is greater than one.

In Example 6, the processor of any one or more of Examples 1-5 is optionally configured to decrease the AV delay from the first extended AV delay to the first AV delay after a third condition is satisfied.

In Example 7, the third condition of any one or more of Examples 1-6 optionally includes an occurrence of a specified number of ventricular paced events before a specified number of ventricular sensed events at the first extended AV delay, wherein the specified number of ventricular paced events is greater than one.

In Example 8, the processor of any one or more of Examples 1-7 is optionally configured to decrease the AV delay from the second extended AV delay to the first AV delay after a fourth condition is satisfied.

In Example 9, the fourth condition of any one or more of Examples 1-8 optionally includes an occurrence of a specified number of ventricular paced events during a specified number of cardiac cycles at the second extended AV delay.

In Example 10, the second extended AV delay of any one or more of Examples 1-9 is optionally substantially equal in duration to the first extended AV delay.

In Example 11, at least one of the first extended AV delay or the second extended AV delay of any one or more of Examples 1-10 optionally includes a fixed-value extended AV delay.

In Example 12, the MTR of any one or more of Examples 1-11 optionally includes a maximum time between a ventricular event of a first cardiac cycle and a ventricular event of a second cardiac cycle, wherein the PVARP includes a refractory period following the ventricular event of the first cardiac cycle, and wherein at least one of the first extended AV delay or the second extended AV delay is greater than the MTR minus the PVARP.

In Example 13, a method includes receiving an atrial event, receiving a ventricular event including at least one of a ventricular paced event or a ventricular sensed event, and providing an atrioventricular (AV) delay using information about the atrial event and the information about the ventricular event, the providing including increasing the AV delay from a first AV delay to a first extended AV delay after a first condition is satisfied to allow a heart to regain intrinsic control of ventricular activation, changing the AV delay from the first extended AV delay to a second extended AV delay after a second condition is satisfied to allow the heart to remain in intrinsic control of ventricular activation, and wherein at least one of the increasing the AV delay to a first extended AV delay or the changing the AV delay to the second extended AV delay includes violating a constraint established using a maximum tracking rate (MTR) and a post ventricular atrial refractory period (PVARP).

In Example 14, the increasing the AV delay to the first extended AV delay after the first condition is satisfied of Example 13 optionally includes after at least one of an occurrence of a specified number of cardiac cycles, after a passing of a specified period of time, or after an occurrence of a ventricular sensed event at the first AV delay.

In Example 15, the increasing the AV delay after the occurrence of the specified number of cardiac cycles of any one or more of Examples 13-14 optionally includes after a preset number of cardiac cycles to allow a regular chance to cease ventricular pacing, and wherein the increasing the AV delay after the passing of the specified number of cardiac cycles includes after a preset time interval to allow a regular chance to cease ventricular pacing.

In Example 16, the changing from the first extended AV delay to the second extended AV delay after the second condition is satisfied of any one or more of Examples 13-15 optionally includes after an occurrence of a specified number of ventricular sensed events before a specified number of ventricular paced events at the first extended AV delay.

In Example 17, the method of any one or more of Examples 13-16 optionally includes decreasing the AV delay from the first extended AV delay to the first AV delay after a third condition is satisfied, the third condition including an occurrence of a specified number of ventricular paced events before a specified number of ventricular sensed events at the first extended AV delay.

In Example 18, the method of any one or more of Examples 13-17 optionally includes decreasing the AV delay from the second extended AV delay to the first AV delay after a fourth condition is satisfied, the fourth condition including an occurrence of a specified number of ventricular paced events during a specified number of cardiac cycles at the second extended AV delay.

In Example 19, the changing the AV delay from the first extended AV delay to the second extended AV delay of any one or more of Examples 13-18 optionally includes changing to an AV delay having a substantially equal duration to the first extended AV delay.

In Example 20, at least one of the increasing the AV delay to a first extended AV delay or the changing the AV delay to the second extended AV delay of any one or more of Examples 13-19 optionally includes increasing or changing the AV delay to a fixed-value extended AV delay.

In Example 21, the MTR of any one or more of Examples 13-20 optionally includes a maximum time between a ventricular event of a first cardiac cycle and a ventricular event of a second cardiac cycle, wherein the PVARP of any one or more of Examples 13-20 optionally includes a refractory period following the ventricular event of the first cardiac cycle, and wherein at least one of the increasing the AV delay to a first extended AV delay or the changing the AV delay to the second extended AV delay of any one or more of Examples 13-20 optionally includes increasing or changing the AV delay to an interval greater than the MTR minus the PVARP.

In Example 22, a system includes an implantable medical device and a processor. The implantable medical device can include an atrial sensing channel configured to receive an atrial event, and a ventricular sensing channel configured to receive a ventricular event including at least one of a ventricular paced event or a ventricular sensed event. The processor can be configured to provide an atrioventricular (AV) delay using information from the atrial sensing channel and the ventricular sensing channel, wherein the processor can be configured to (1) provide a first AV delay and remain at the first AV delay until a first condition is satisfied, the first condition including at least one of an occurrence of a specified number of cardiac cycles, a passing of a specified period of time, or an occurrence of a ventricular sensed event at the first AV delay at the first AV delay, (2) provide, after the first condition is satisfied at the first AV delay, a first extended AV delay to allow a heart to regain intrinsic control of ventricular activation and remain at the first extended AV delay until a second condition or a third condition is satisfied, the second condition including an occurrence of a specified number of ventricular sensed events before a specified number of ventricular paced events at the first extended AV delay, and the third condition including an occurrence of a specified number of ventricular paced events before a specified number of ventricular sensed events at the first extended AV delay, (3) provide, after the second condition is satisfied at the first extended AV delay, a second extended AV delay to allow the heart to remain in intrinsic control of ventricular activation and remain at the second extended AV delay until a fourth condition is satisfied, the fourth condition including an occurrence of a specified number of ventricular paced events during a specified number of cardiac cycles at the second extended AV delay; and (4) provide, after the third condition is satisfied at the first extended AV delay or the fourth condition is satisfied at the second extended AV delay, the first AV delay and remain at the first AV delay until the first condition is satisfied. In Example 22, at least one of the first extended AV delay or the second extended AV delay can violate a constraint established using a maximum tracking rate (MTR) and a post ventricular atrial refractory period (PVARP).

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Generally, dual chamber pacing includes pacing where energy is delivered to both the atrium and the ventricle. The atrioventricular (AV) delay interval, as used herein, refers to the interval between an atrial event (e.g., an atrial pace or an atrial sense, usually the right atrium) and a first ventricular pace to one of the ventricles (e.g., a right ventricle). The AV delay interval can be the same or different depending upon whether it is initiated by an atrial sense or an atrial pace (e.g., in atrial tracking mode or AV sequential pacing mode, respectively). Bi-ventricular pacing includes pacing both the left ventricle and the right ventricle. The biventricular offset (BVO) interval, as used herein, refers to the interval between the first ventricular pace and a second ventricular pace to the other ventricle (e.g., the left ventricle) during the same cardiac cycle. One approach to bi-ventricular pacing includes specifying an AV delay interval and a BVO interval. Another approach to bi-ventricular pacing includes specifying a separate AV delay interval for each ventricle, which can be designated as AVDR for the right ventricle and AVDL for the left ventricle. Generally, for subjects having intact or normally functioning AV conduction pathways, the later-paced ventricle will be paced, if at all, close to the time at which that ventricle is intrinsically activated, such as to achieve an optimal or desired preloading. In subjects having normal AV conduction, the optimal or desired AVD and BVO intervals can be related to both the intrinsic atrioventricular interval and the amount of pre-excitation time needed for one ventricle relative to the other (e.g., the extent of the ventricular conduction deficit).

Generally, a cardiac rhythm or function management device can be configured to detect one or more type of cardiac arrhythmia, such as an atrial or ventricular fibrillation or tachycardia. In certain examples, using shocking electrodes in one or more configurations, an implantable medical device can be configured to deliver a defibrillation energy configured to depolarize a critical mass of a heart, terminate the cardiac arrhythmia, and allow a normal sinus rhythm to be reestablished.

In certain examples, the implantable medical device can include an implantable defibrillator, or an implantable pacemaker or other cardiac rhythm or unction management device having a defibrillation backup or other defibrillation energy delivery mode.

Figure 1:
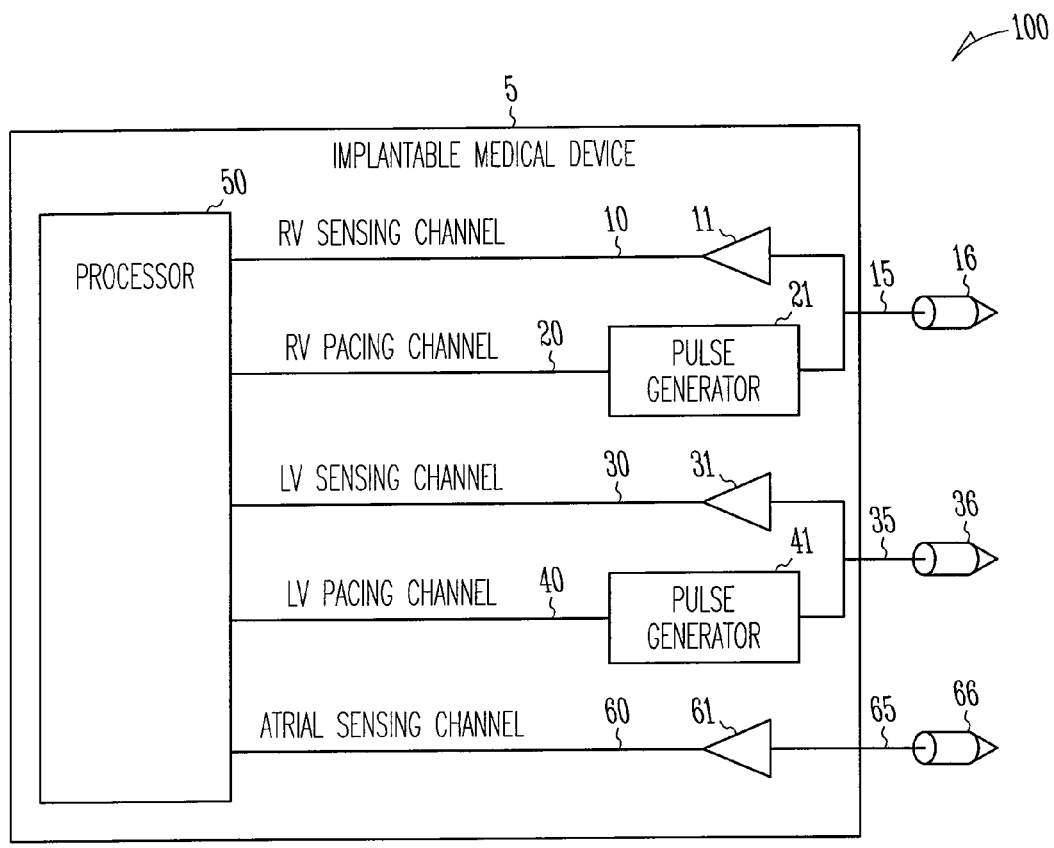
FIGS. 1, 2, and 5 illustrate generally examples of systems or portions of a system for delivering cardiac therapy.

FIG. 1 illustrates generally an example of a system 100 for delivering cardiac therapy. In an example, the system 100 can include an implantable medical device (IMD) 5 having a processor 50, a right ventricular sensing channel 10, a right ventricular pacing channel 20, a left ventricular sensing channel 30, a left ventricular pacing channel 40, and an atrial sensing channel 60. The atrial sensing channel 60 can include at least one of a right atrial sensing channel or a left atrial sensing channel. In other examples, the IMD 5 can include a combination of at least one of the a right ventricular sensing channel 10, the right ventricular pacing channel 20, the left ventricular sensing channel 30, the left ventricular pacing channel 40, or the atrial sensing channel 60.

In certain examples, the right ventricular sensing channel 10 can include a sense amplifier 11, the left ventricular sensing channel 30 can include a sense amplifier 31, the right ventricle pacing channel 20 can include a pulse generator 21, the left ventricular pacing channel 40 can include a pulse generator 41, and the atrial sensing channel 60 can include a sense amplifier 61. In other examples, the right ventricular sensing channel 10 or the right ventricular pacing channel 20 can be coupled to an electrode 16 disposed on a lead 15 or elsewhere, the left ventricular sensing channel 30 or the left ventricular pacing channels 40 can be coupled to an electrode 36 disposed on a lead 35 or elsewhere, or the atrial sensing channel 60 can be coupled to an electrode 66 disposed on a lead 65 or elsewhere.

In certain examples, the lead 15 can be configured to electrically couple the sense amplifier 11 or the pulse generator 21 to the electrode 16, which can be configured to be located in a right ventricle, such as in the septal region, the free wall region, or another region of the right ventricle. Similarly, the lead 35 can be configured to electrically couple the sense amplifier 31 or the pulse generator 41 to the electrode 36, which can be configured to be located in, on, or near a left ventricle, such as in the septal region, the free wall region, or another region of the left ventricle or in the coronary vasculature. Further, the lead 65 can be configured to electrically couple the sense amplifier 61 to the electrode 66, which can be configured to be located in at least one of a right atrium or a left atrium of the subject 101.

In certain examples, the implantable medical device 5 can include one or more other pacing or sensing channels, such as an internal thoracic pacing or sensing channel configured to couple the processor 50 to an internal thoracic location external to the heart (e.g., through one or more leads, electrodes, pulse generators, or sense amplifiers). In an example, the internal thoracic pacing or sensing channel can be configured to send or receive information to or from a housing can electrode, located on the exterior housing of an implantable medical device located in the internal thoracic location external to the heart.

In the example of FIG. 1, the processor 50 can be an implantable component, an external component, or a combination or permutation of an implantable processor and an external processor. In an example, if at least a portion of the processor 50 includes an external processor, then the processor 50 can be configured to be communicatively coupled (such as via telemetry, RF, or other communication protocol) with the remaining implantable components (such as the sense amplifier 11, 31, the pulse generator 21, 41, the lead 15, 35, or the electrode 16, 36). In an example, the implantable processor can be configured to have reduced or minimal functionality or power consumption. In certain examples, it can be advantageous for the processor 50 to include an external processor for computing complex operations, such as to compute an AV delay interval. In other examples, the external processor can include an external device that can be either local or remote. In an example, the processor 50 can include a microcontroller, a microprocessor, a logic circuit, or other processor.

Figure 2:
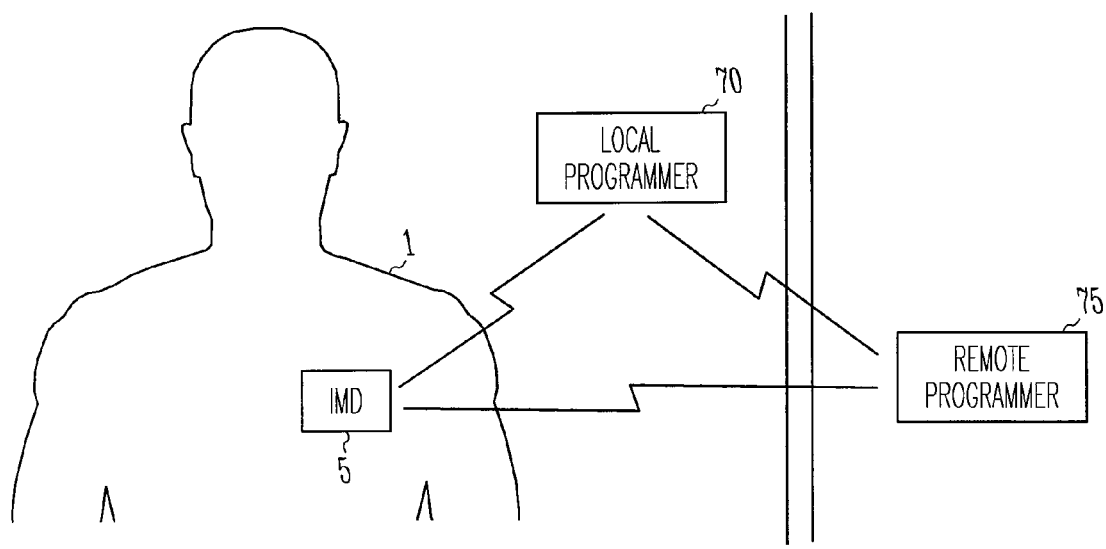

FIG. 2 illustrates generally an example of a portion of a system 200 including an IMD 5 configured to be implanted in a subject 101. The system 200 can include at least one of a local programmer 70 or a remote programmer 75. Both the local programmer 70 and the remote programmer 75 are external components. In an example, the local programmer 70 can include a hand-held programmer or other programmer capable of being positioned in communication proximity to the processor 50. The proximity range between the processor 50 and the local programmer 70 can vary depending upon the type of data communication and is bound by the physical constraints of the communication type. In an example, the remote programmer 75 can include any programmer configured to communicate with the IMD 5 either directly or indirectly (such as through another device, e.g., a router, the local programmer 70, etc.). In various examples, the remote programmer 75 can be configured to communicate with or store information from a plurality of implanted or external devices, and the remote programmer 75 can be configured to be located a long distance from the subject 1.

In an example, the local programmer 70 or the remote programmer 75 can be configured to send information to or receive information from the IMD 5. The information can include programming information, subject data, device data, or other instructions, alerts, or other information. Further, the local programmer 70 or the remote programmer 75 can be configured to communicate the sent or received information to a user or physician, such as by sending an alert via email of the status of the subject 1 or the system components.

Extended AV Delay

Figure 3:
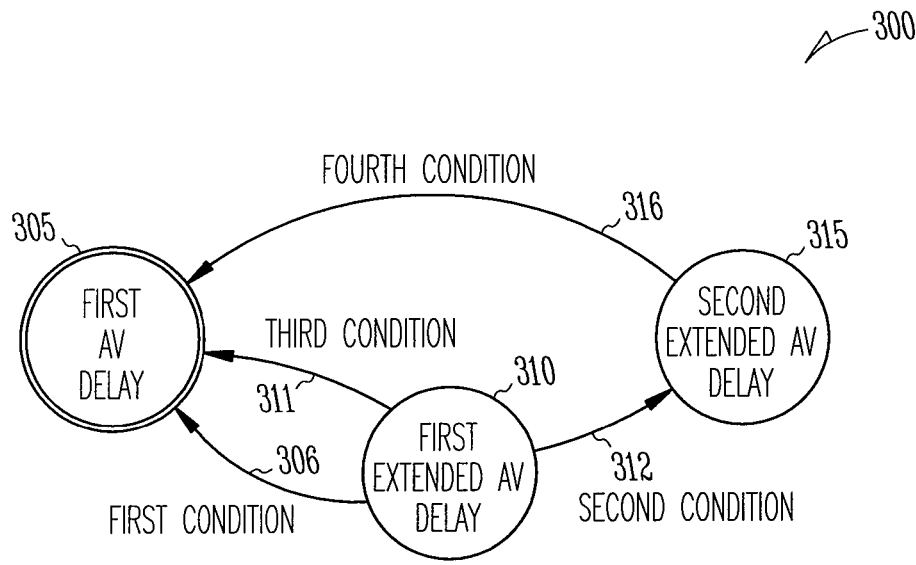
FIG. 3 illustrates generally an example of a state diagram illustrating switching between a first AV delay, a first extended AV delay, and a second extended AV delay.

FIG. 3 illustrates generally an example of a state diagram 300 illustrating switching between a first AV delay 305, a first extended AV delay 310, and a second extended AV delay 315. Pacing a heart using the first extended AV delay 310 or the second AV extended delay 315 can allow the heart to regain intrinsic control of ventricular activations below the first extended AV delay 310 or the second extended AV delay 315. In certain examples, the first AV delay 305 can include a fixed interval, e.g., an AV delay interval established by a clinician or a device using physiological data of the subject. In certain examples, the first AV delay 305 can include a dynamic interval, e.g., an AV delay interval established, updated, or otherwise modulated using physiological data from the subject 1.

In certain examples, the first AV delay 305 can be calculated as an optimal AV delay, such as disclosed in the commonly assigned Ding et al. U.S. Pat. No. 7,013,176 entitled, "METHOD AND APPARATUS FOR SETTING PACING PARAMETERS IN CARDIAC RESYNCHRONIZATION THERAPY," (herein "the Ding et al. '176 patent") the commonly assigned Ding et al. U.S. Pat. No. 7,203,540 entitled, "METHOD AND SYSTEM FOR SETTING CARDIAC RESYNCHRONIZATION THERAPY PARAMETERS," (herein "the Ding et al. '540 patent") or the commonly assigned Ding et al. U.S. Pat. No. 7,123,960 entitled, "METHOD AND SYSTEM FOR DELIVERING CARDIAC RESYNCHRONIZATION THERAPY WITH VARIABLE ATRIO-VENTRICULAR DELAY," (herein "the Ding et al. '960 patent") the disclosures of which are each incorporated by reference in their entirety, including their disclosure of computing an optimal AV delay interval. In other examples, other techniques of calculating the first AV delay interval can be used.

In the example of FIG. 3, the first extended AV delay 310 and the second extended AV delay 315 can include fixed values. In an example, the first extended AV delay 310 or the second extended AV delay 315 can be established by a clinician. In various examples, the first extended AV delay 310 can be established as the same value or a different value as the second extended AV delay 315. The present inventors have recognized, among other things, that a fixed-value extended AV delay interval can provide a simple, low power, well-defined, recognizable extended AV delay interval (e.g., in contrast to a dynamic extended AV delay). In certain examples, the extended AV delay interval can be fixed at a value that would violate certain conditions placed on other non-fixed-value AV delay calculations. For example, a clinician may not recognize a value or an occurrence of an extended AV delay interval that is established as a function of a normal AV delay interval. Moreover, establishing the extended AV delay interval as a function of the normal AV delay interval requires processing power, and the resulting extended AV delay interval can be bound by certain conditions. However, by fixing the first extended AV delay 310 or the second extended AV interval 315, the clinician can more easily recognize an occurrence of an extended AV delay interval at the fixed value. In certain examples, the fixed-value extended AV delay interval can be established using less processing power. The fixed-value extended AV delay interval can also be permitted to violate certain constraints that are sometimes imposed on variable-value extended AV delay intervals. In an example, the clinician can specify the fixed-value of the first extended AV delay 310 or the second extended AV delay 315 such that one or both intervals can exceed the normal boundary established by the MTR and the post ventricular atrial refractory period (PVARP), the relationship of which shown in FIG. 4.

In an example, the first AV delay 305 transitions to the extended AV delay 310 after a first condition 306 is satisfied, such as after the occurrence of a cardiac cycles. The a cardiac cycles can include a fixed, pre-determined, or otherwise established number of cardiac cycles, e.g., 32 cardiac cycles, 64 cardiac cycles, etc. Establishing a regular fixed entry condition to the first extended AV delay 310, such as every a cardiac cycles or one or more other regular conditions (e.g., a specified time interval, etc.), can allow for a regular chance to cease ventricular pacing and allow the heart to regain intrinsic control of ventricular activations. Other entry conditions into an extended AV delay can include the occurrence of one or more intrinsic activations occurring within the first AV delay 305, which can establish irregular or infrequent chances to cease ventricular pacing and allow for the heart to regain intrinsic control of ventricular activations. Using the regular fixed entry condition (e.g., a cardiac cycles) can provide for a more regularly engaged or more robust transition from the first AV delay 305 to the first extended AV delay 310. In certain examples, the first condition 306 can include the occurrence of consecutive intrinsic activations, or the first condition 306 can include the occurrence of non-consecutive intrinsic activations in a specified number of cardiac cycles (e.g., 2 intrinsic activations in three cardiac cycles, etc.).

In certain examples, the first extended AV delay 310 can transition back to the first AV delay 305 or transition to the second extended AV delay 315. In an example, the first extended AV delay 310 can transition back to first AV delay 305 after a third condition 311 is satisfied, such as b ventricular paces in the first extended AV delay 310. The b ventricular paces can include a fixed, pre-determined, or otherwise established number of ventricular paces, e.g., 4, 8, 16, etc. In certain examples, the b ventricular paces can include consecutive ventricular paces. However, in other examples, the b ventricular paces can include non-consecutive ventricular paces, for example, to provide a more robust exit condition. The ventricular paces can include sensed ventricular paces. In this example, the third condition 311 can include a number of b ventricular paces higher than 1, and in certain examples, a significant amount of ventricular paces higher than 1 (e.g., 4, 8, 16, etc.). In an example, the third condition 311 can allow for the heart to incrementally regain intrinsic control by a more robust exit criteria from the first extended AV delay 310, for example, as opposed to requiring consecutive ventricular senses to enter or remain at an extended AV delay.

In another example, the first extended AV delay 310 can transition to the second extended AV delay 315 after a second condition 312 is satisfied, such as a ventricular sensed activation. The ventricular sensed activation can include a specified number of ventricular sensed activations (e.g., one or more consecutive or non-consecutive ventricular sensed activations) occurring before the b ventricular paces is satisfied. In certain examples, because the b ventricular paces can include a number of ventricular paces higher than 1, and because the b ventricular paces can be non-consecutive, the second condition 312 can provide a more robust entry criteria to the second extended AV delay 315, for example, as opposed to requiring consecutive ventricular senses to enter the second extended AV delay 315.

The entry condition for the transition from the first extended AV delay 310 to the first AV delay 305 can be more stringent than for the transition from the second extended AV delay 315 to the first AV delay 305. This can encourage a tendency to remain in the second extended AV delay 315, which, in turn, can allow the heart more opportunity to intrinsically control the ventricular activations. In an example, the second extended AV delay 315 can transition to the first AV delay 305 after a fourth condition 316 is satisfied, such as the occurrence of c ventricular paces in d cardiac cycles. The c ventricular paces in d cardiac cycles can include a fixed, predetermined, or otherwise established number of ventricular paces out of a fixed, predetermined, or otherwise established number of cardiac cycles (d), e.g., 2 ventricular paces out of the last 10 cardiac cycles (2 ventricular paces/10 cardiac cycles, etc.). In certain examples, the c ventricular paces can include consecutive ventricular paces. However, in other examples, the c ventricular paces can include non-consecutive ventricular paces, for example, to provide a more robust exit condition. Like above with respect to the second condition 312 and the third condition 311, in certain examples, the fourth condition 316 can provide a more robust exit criteria from the second extended AV delay 315 to the first AV delay 305, for example, by not requiring consecutive ventricular senses or paces.

Figure 4:
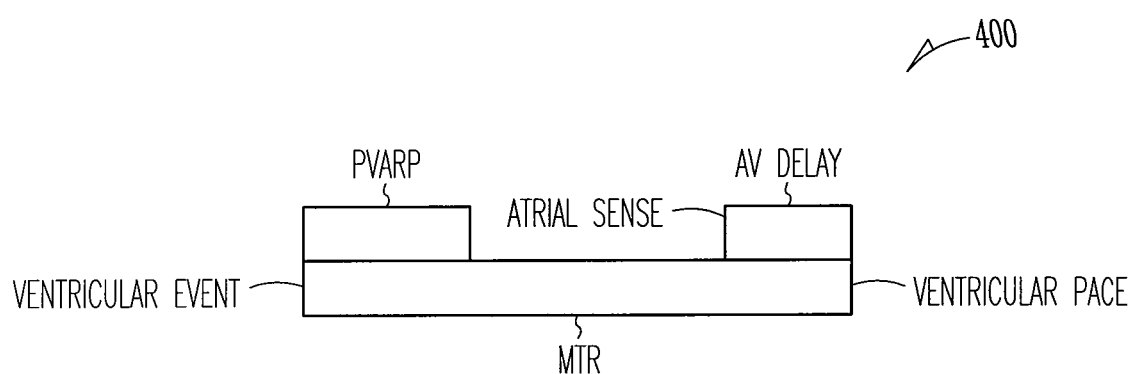
FIG. 4 illustrates generally an example of a timing diagram illustrating a relationship between a maximum tracking rate (MTR) (or upper rate limit (URL)), a post ventricular atrial refractory period (PVARP), and an AV delay.

FIG. 4 illustrates generally an example of a timing diagram 400 illustrating a relationship between a maximum tracking rate (MTR) (or upper rate limit (URL)), a post ventricular atrial refractory period (PVARP), and an AV delay. The MTR is a maximum pacing rate determined by a clinician or calculated using physiological data of the subject 1. The PVARP is an interval following a ventricular event during which atrial-like events (e.g., retrograde P waves, far-field R waves, premature atrial contractions, etc.) are ignored for the purposes of beginning an AV delay. The timing diagram 400 includes a MTR beginning with a ventricular event and ending with a ventricular pace. The ventricular event can include a ventricular pace or a ventricular sensed activation. If a ventricular sensed activation does not occur following a ventricular event of the previous cardiac cycle during a pre-set or otherwise established interval, such as the MTR, then the ventricle is paced. Thus, absent a ventricular sensed activation, the MTR is the time between a ventricular event of a first cardiac cycle and a ventricular pace of a second cardiac cycle. Generally, the AV delay (e.g., the first AV delay 305 or the extended AV delay 310, 315) is constrained by the relationship between the MTR and the PVARP (e.g., AV≦MTR−PVARP). In an example, the first AV delay 305 adheres to this relationship. However, in other examples, a clinician can violate this relationship by fixing the first extended AV delay 310 or the second extended AV delay 315 to be beyond the given relationship.

LV Unipolar Sensing or Pacing Vector

In an example, an AV delay can be calculated using an intrinsic atrioventricular interval $AV_R$ (the interval between an intrinsic atrial activation and an intrinsic right ventricular activation) or an intrinsic atrioventricular interval $AV_L$, (the interval between an intrinsic atrial activation and an intrinsic left ventricular activation), such as is disclosed in the above-incorporated Ding et al. '176 patent, the above-incorporated Ding et al. '540 patent, or the above-incorporated Ding et al. '960 patent. In certain examples, the intrinsic atrial activation can be sensed using the electrode 66 coupled to the atrial sensing channel 60 of the IMD 5, the intrinsic left ventricular activation can be sensed using the electrode 36 coupled to the LV sensing channel 30 of the IMD 5, or the intrinsic right ventricular activation can be sensed using the electrode 16 coupled to the RV sensing channel 10 of the IMD 5. In an example, the processor 50 can be configured to compute the $AV_R$ or the $AV_L$ using at least one of the sensed intrinsic atrial activation, the sensed intrinsic right ventricular activation, or the sensed intrinsic left ventricular activation.

Figure 5:
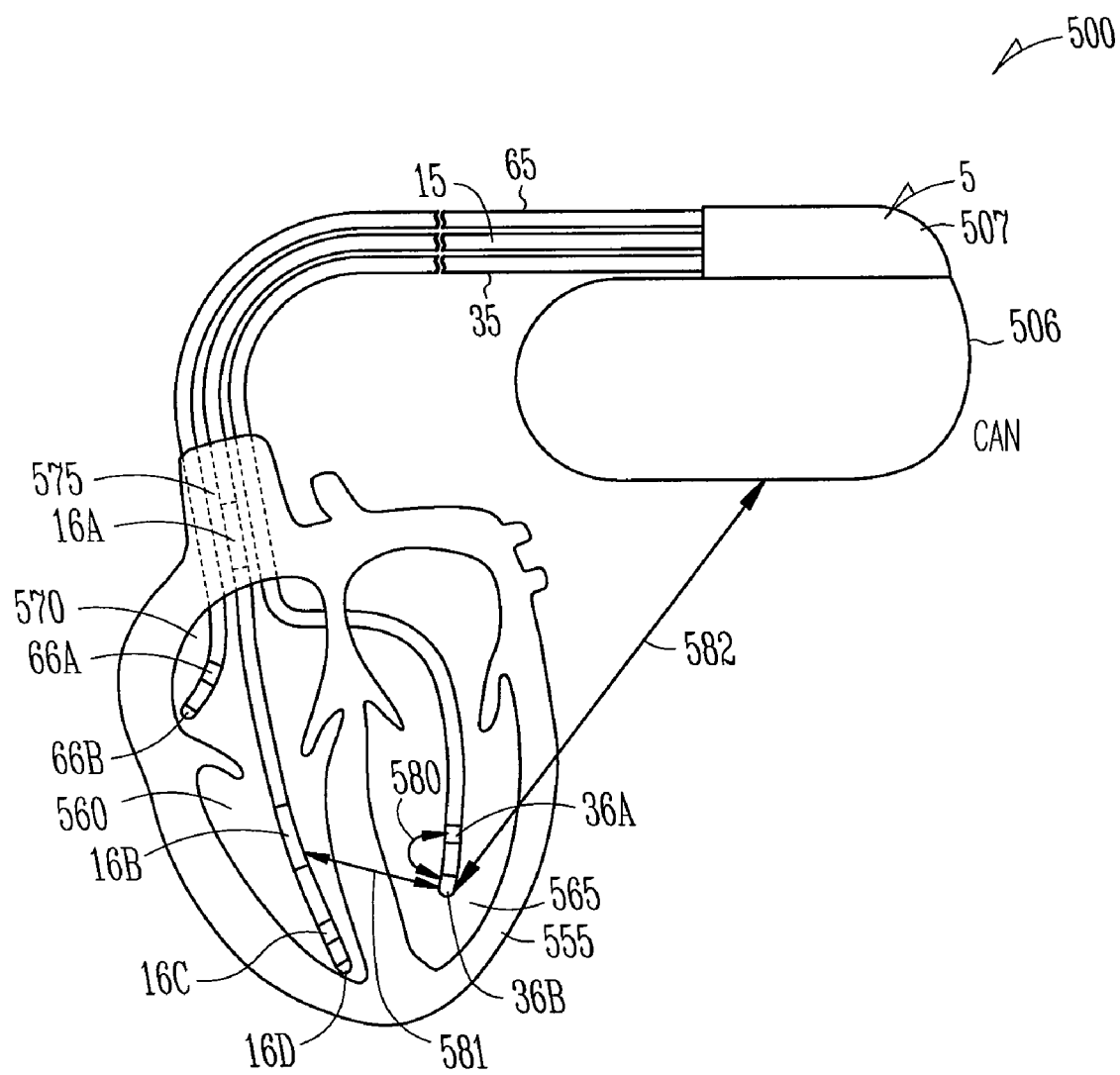

FIG. 5 illustrates generally an example of portions of a system 500 including an IMD 5, an RV lead 15, an LV lead 35, an atrial lead 65, and a heart 555. The IMD 5 can include a housing 506 (or CAN), and a header 507. In an example, at least a portion of the exterior of the housing 506 can include an electrode, herein referred to as the housing can electrode.

The RV lead 15 can include a first electrode 16a configured to be located in the superior vena cava 575 of the heart 555, and a second electrode 16b, a third electrode 16b, and a fourth electrode 16d configured to be located in the right ventricle 560 of the heart 555. In an example, one or more electrodes, such as the first electrode 16a or the second electrode 16b, can include a shocking coil electrode configured to deliver a high energy shock (e.g., 0.1 Joule or greater, etc.) to the heart. In certain examples, the first electrode 16a can include a proximal defibrillation coil electrode and the second electrode 16b can include a distal defibrillation coil electrode.

The LV lead 35 can include a fifth electrode 36a and a sixth electrode 36b configured to be located in, on, or near the left ventricle 565 of the heart 555, such as within the coronary vasculature. In an example, the sixth electrode 36b can include a distal pacing or sensing electrode. The atrial lead 65 can include a seventh electrode 66a and an eighth electrode 66b configured to be located in the right atrium 570 of the heart 555. In certain examples, the housing can electrode can be electrically coupled to at least one other electrode (e.g., the first electrode 16a), or the housing can electrode can be electrically isolated from other electrodes and capable of independent control. Further, in certain examples, the first electrode 16a through the eighth electrode 66b can include at least one of a coil-type electrode, a ring-type electrode, or a tip electrode.

In certain examples, the RV lead 15 can be configured to electrically couple the IMD 5 to at least one of the right ventricle 560, the right atrium 570, or the superior vena cava 575 using at least one electrode (e.g., the first electrode 16a, the second electrode 16b, the third electrode 16c, or the fourth electrode 16d), the LV lead 35 can be configured to electrically couple the IMD 5 to the left ventricle 565 using at least one electrode (e.g., the fifth electrode 36a or the sixth electrode 36b), or the atrial lead 65 can be configured to electrically couple the IMD 5 to the right ventricle 570 using at least one electrode (e.g., the seventh electrode 66a or the eighth electrode 66b). In an example, at least one of the second electrode 16b, the third electrode 16c, or the fourth electrode 16, can be configured to be located in, on, or near a right apical region of the heart 555. In other examples, the fifth electrode 36a or the sixth electrode 36b can be configured to be located in, on, or near a left apical region of the heart 555 or a left ventricular free lateral wall of the heart 555.

In an example, the left ventricular activation can be sensed, such as to calculate an AV delay interval or other pacing interval or parameter, or for other desired purpose in cardiac function management, such as cardiac arrhythmia detection. The left ventricular activation can be sensed using a sensing vector defined by the particular electrodes used for performing the sensing. In certain examples, the sensing vector can include a bipolar sensing vector 580, the bipolar sensing vector 580 including a sensing vector between a left ventricular tip electrode, such as the sixth electrode 36b, and a left ventricular ring electrode, such as the fifth electrode 36a, or an extended bipolar sensing vector 581, the extended bipolar sensing vector 581 including a sensing vector between a left ventricular tip electrode, such as the sixth electrode 36b, and a right ventricular distal electrode, such as the second electrode 16b or the third electrode 16c. However, the present inventors have recognized, among other things, that sensing the left ventricular activation using the bipolar sensing vector 580 or extended bipolar sensing vector 581 can potentially lead to oversensing the right ventricular activation, or more generally, sensing something other than the left ventricular activation. Moreover, the present inventors have recognized, among other things, that it can be difficult or impossible to determine if oversensing is occurring in various implantable systems (e.g., due to differences in available sensing vectors, etc.). Thus, to avoid the oversensing or the uncertainty of using the bipolar sensing vector 580 or the extended bipolar sensing vector 581, the left ventricular activation can be sensed using a unipolar sensing vector 582, the unipolar sensing vector 582 including a vector between a left ventricular electrode, such as the fifth electrode 36a or the sixth electrode 36b, and a housing can electrode. In other examples, the one or more other sensing vectors can be defined using one or more right atrial electrodes, one or more right ventricular electrodes, or one or more other electrodes, and a housing can electrode, creating a right atrium to housing can unipolar sensing vector, a right ventricle to housing can unipolar sensing vector, or one or more other unipolar sensing vectors.

In certain examples, a cardiac rhythm management device capable of delivering a defibrillation energy can include a shocking electrode, such as the first electrode 16a, electrically tied or coupled to the housing can electrode. In this example, having the housing can electrode electrically tied or coupled to one or more other electrodes can eliminate the possibility of using the unipolar sensing vector 582 due to the added vector between the left ventricular electrode and the shocking electrode.

In an example, the IMD 5 can automatically switch to using the unipolar sensing vector 582 to detect, sense, measure, or calculate a left ventricular activation, e.g., to calculate the AV delay interval or other pacing intervals or parameters, or for other cardiac function management purpose, such as to avoid the oversensing or the uncertainty of using the bipolar sensing vector 580 or the extended bipolar sensing vector 581. However, when a defibrillation energy is desired, the IMD 5 can be configured to electrically or mechanically couple the first electrode 15 or one or more other electrode to the housing can electrode to deliver a defibrillation energy to the heart.

In other examples, a pacing or other stimulation energy can be delivered using the unipolar sensing vector 582 or one or more other unipolar sensing vectors (e.g., right ventricle to housing can unipolar vector, etc.).

In an example, if a right ventricular electrode fails, such as a right ventricular ring electrode, then a right ventricle to housing can unipolar vector (e.g., using a right ventricular tip electrode and the housing can electrode) can be used, for example, in to sense a right ventricular activation in place of using the failed electrode in conjunction with one or more other electrodes.

In certain examples, an atrial lead can have a lower cost than a ventricular lead. In an example, a right atrium to housing can unipolar vector can be used, for example, to reduce the overall cost of the system, or in place of a failed left ventricular or other electrode.

Additional Notes

The above detailed description includes references to the accompanying drawings, which form a part of the detailed description. The drawings show, by way of illustration, specific embodiments in which the invention can be practiced.

These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
an implantable medical device including:
an atrial sensing channel configured to receive an atrial event; and
a ventricular sensing channel configured to receive a ventricular event including at least one of a ventricular paced event or a ventricular sensed event;
a processor configured to provide an atrioventricular (AV) delay using information from the atrial sensing channel and the ventricular sensing channel, wherein the processor is configured to increase the AV delay from a first AV delay to a first extended AV delay after a first condition is satisfied to allow a heart to regain intrinsic control of ventricular activation, and wherein the processor is configured to change the AV delay from the first extended AV delay to a second extended AV delay after a second condition is satisfied to allow the heart to remain in intrinsic control of ventricular activation; and wherein at least one of the first extended AV delay or the second extended AV delay violates a constraint established using a maximum tracking rate (MTR) and a post ventricular atrial refractory period (PVARP).

2. The system of claim 1, wherein the first condition includes at least one of an occurrence of a specified number of cardiac cycles, a passing of a specified period of time, or an occurrence of a ventricular sensed event at the first AV delay.

3. The system of claim 2, wherein the specified number of cardiac cycles includes a preset number of cardiac cycles configured to allow a regular chance to cease ventricular pacing; and wherein the specified period of time includes a preset time interval configured to allow a regular chance to cease ventricular pacing.

4. The system of claim 1, wherein the second condition includes an occurrence of a specified number of ventricular sensed events before a specified number of ventricular paced events at the first extended AV delay.

5. The system of claim 4, wherein the second condition includes a single ventricular sense event before the specified number of ventricular paced events at the first extended AV delay, wherein the specified number of ventricular paced events is greater than one.

6. The system of claim 1, wherein the processor is configured to decrease the AV delay from the first extended AV delay to the first AV delay after a third condition is satisfied.

7. The system of claim 6, wherein the third condition includes an occurrence of a specified number of ventricular paced events before a specified number of ventricular sensed events at the first extended AV delay, wherein the specified number of ventricular paced events is greater than one.

8. The system of claim 1, wherein the processor is configured to decrease the AV delay from the second extended AV delay to the first AV delay after a fourth condition is satisfied.

9. The system of claim 8, wherein the fourth condition includes an occurrence of a specified number of ventricular paced events during a specified number of cardiac cycles at the second extended AV delay.

10. The system of claim 1, wherein the second extended AV delay is substantially equal in duration to the first extended AV delay.

11. The system of claim 1, wherein at least one of the first extended AV delay or the second extended AV delay includes a fixed-value extended AV delay.

12. The system of claim 1, wherein the MTR includes a maximum time between a ventricular event of a first cardiac cycle and a ventricular event of a second cardiac cycle, wherein the PVARP includes a refractory period following the ventricular event of the first cardiac cycle, and wherein at least one of the first extended AV delay or the second extended AV delay is greater than the MTR minus the PVARP.

13. A method comprising:
receiving an atrial event;
receiving a ventricular event including at least one of a ventricular paced event or a ventricular sensed event; and
providing an atrioventricular (AV) delay using information about the atrial event and the information about the ventricular event, the providing including:
increasing the AV delay from a first AV delay to a first extended AV delay after a first condition is satisfied to allow a heart to regain intrinsic control of ventricular activation;

changing the AV delay from the first extended AV delay to a second extended AV delay after a second condition is satisfied to allow the heart to remain in intrinsic control of ventricular activation; and wherein at least one of the increasing the AV delay to a first extended AV delay or the changing the AV delay to the second extended AV delay includes violating a constraint established using a maximum tracking rate (MTR) and a post ventricular atrial refractory period (PVARP).

14. The method of claim 13, wherein the increasing the AV delay to the first extended AV delay after the first condition is satisfied includes after at least one of an occurrence of a specified number of cardiac cycles, after a passing of a specified period of time, or after an occurrence of a ventricular sensed event at the first AV delay.

15. The method of claim 14, wherein the increasing the AV delay after the occurrence of the specified number of cardiac cycles includes after a preset number of cardiac cycles to allow a regular chance to cease ventricular pacing; and wherein the increasing the AV delay after the passing of the specified number of cardiac cycles includes after a preset time interval to allow a regular chance to cease ventricular pacing.

16. The method of claim 13, wherein the changing from the first extended AV delay to the second extended AV delay after the second condition is satisfied includes after an occurrence of a specified number of ventricular sensed events before a specified number of ventricular paced events at the first extended AV delay.

17. The method of claim 13, including decreasing the AV delay from the first extended AV delay to the first AV delay after a third condition is satisfied, the third condition including an occurrence of a specified number of ventricular paced events before a specified number of ventricular sensed events at the first extended AV delay.

18. The method of claim 13, including decreasing the AV delay from the second extended AV delay to the first AV delay after a fourth condition is satisfied, the fourth condition including an occurrence of a specified number of ventricular paced events during a specified number of cardiac cycles at the second extended AV delay.

19. The method of claim 13, wherein the changing the AV delay from the first extended AV delay to the second extended AV delay includes changing to an AV delay having a substantially equal duration to the first extended AV delay.

20. The method of claim 13, wherein at least one of the increasing the AV delay to a first extended AV delay or the changing the AV delay to the second extended AV delay includes increasing or changing the AV delay to a fixed-value extended AV delay.

21. The method of claim 13, wherein the MTR includes a maximum time between a ventricular event of a first cardiac cycle and a ventricular event of a second cardiac cycle, wherein the PVARP includes a refractory period following the ventricular event of the first cardiac cycle, and wherein at least one of the increasing the AV delay to a first extended AV delay or the changing the AV delay to the second extended AV delay includes increasing or changing the AV delay to an interval greater than the MTR minus the PVARP.

22. A system comprising:
an implantable medical device including:
an atrial sensing channel configured to receive an atrial event; and
a ventricular sensing channel configured to receive a ventricular event including at least one of a ventricular paced event or a ventricular sensed event;

a processor configured to provide an atrioventricular (AV) delay using information from the atrial sensing channel and the ventricular sensing channel, wherein the processor is configured to:
  (1) provide a first AV delay and remain at the first AV delay until a first condition is satisfied, the first condition including at least one of an occurrence of a specified number of cardiac cycles, a passing of a specified period of time, or an occurrence of a ventricular sensed event at the first AV delay;
  (2) provide, after the first condition is satisfied at the first AV delay, a first extended AV delay to allow a heart to regain intrinsic control of ventricular activation and remain at the first extended AV delay until a second condition or a third condition is satisfied, the second condition including an occurrence of a specified number of ventricular sensed events before a specified number of ventricular paced events at the first extended AV delay, and the third condition including an occurrence of a specified number of ventricular paced events before a specified number of ventricular sensed events at the first extended AV delay;
  (3) provide, after the second condition is satisfied at the first extended AV delay, a second extended AV delay to allow the heart to remain in intrinsic control of ventricular activation and remain at the second extended AV delay until a fourth condition is satisfied, the fourth condition including an occurrence of a specified number of ventricular paced events during a specified number of cardiac cycles at the second extended AV delay; and
  (4) provide, after the third condition is satisfied at the first extended AV delay or the fourth condition is satisfied at the second extended AV delay, the first AV delay and remain at the first AV delay until the first condition is satisfied; and
wherein at least one of the first extended AV delay or the second extended AV delay violates a constraint established using a maximum tracking rate (MTR) and a post ventricular atrial refractory period (PVARP).

* * * * *